United States Patent [19]
Orr et al.

[11] Patent Number: 6,059,732
[45] Date of Patent: May 9, 2000

[54] ISO-VOLUMETRIC METHOD OF MEASURING CARBON DIOXIDE ELIMINATION

[75] Inventors: Joseph A. Orr, Park City, Utah; Michael B. Jaffe, Cheshire, Conn.; Kai Kück, Hamburg, Germany; Dinesh G. Haryadi, Bangalore, India

[73] Assignee: NTC Technology, Inc., Wilmington, Del.

[21] Appl. No.: 09/150,447

[22] Filed: Sep. 9, 1998

[51] Int. Cl.[7] .................................................. A61B 5/08
[52] U.S. Cl. ........................... 600/532; 600/538; 600/531
[58] Field of Search ................................... 600/529, 531, 600/532, 538, 533

[56] References Cited

U.S. PATENT DOCUMENTS

| | | | |
|---|---|---|---|
| 4,221,224 | 9/1980 | Clark | 600/531 |
| 4,463,764 | 8/1984 | Anderson et al. | 600/532 |
| 5,060,656 | 10/1991 | Howard | 600/531 |
| 5,069,220 | 12/1991 | Casparie et al. | 600/532 |
| 5,117,674 | 6/1992 | Howard | 600/531 |
| 5,178,155 | 1/1993 | Mault | 600/538 |
| 5,285,794 | 2/1994 | Lynch | 600/532 |
| 5,299,579 | 4/1994 | Gedeon et al. | 600/532 |
| 5,402,796 | 4/1995 | Packer et al. | 600/532 |

FOREIGN PATENT DOCUMENTS

WO 98/12963  4/1998  WIPO .

OTHER PUBLICATIONS

H. Blomquist et al., A Non–Invasive Technique for Measurement of Lung Perfusion, Intensive Care Medicine 1986; 12:172.

R.J. Bosman et al, Non–Invasive Pulimonary Blood Flow Measurement by Means of $CO_2$ Analysis Of Expiratory Gases, Intensive Care Medicine 1991, 17:98–102.

A. Gedeon, Non–Invasive Pulmonary Blood Flow for Optimal Peep, ICOR AB, Ulvsundavagen 178 B, S–161 30 Bromma, Sweden, pp. 49–58.

Capek, J.M. Noninvasive Measurement of Cardiac Output Using Partial $CO_2$ Rebreathing [Dissertation], Rensselaer Polytechnic Institute (1988) 28:351 p. (due to large number of pages, only table of contents and abstract have been copied).

Capek, J.M., et al., Noninvasive Measurements of Cardiac Output Using Partial $CO_2$ Rebreathing, IEEE Trans. Biomed. Eng. (1988) 35(9):653–61.

Davies, Gerald G., et al., Continuous Fick cardiac output compared to thermodilution cadiac output, Critical Care Medicine (1986) 14(10):881–85.

Elliot, C. Gregory, et al., Complications of Pulmonary Artery Catheterization in the Care of Critically Ill Patients, Chest (1979) 76:647–52.

(List continued on next page.)

*Primary Examiner*—Max Hindenburg
*Assistant Examiner*—N Natnithithadha
*Attorney, Agent, or Firm*—Trask, Britt & Rossa

[57] ABSTRACT

A method of calculating the carbon dioxide elimination of a patient that includes counteracting any inaccuracy or inconsistency in respiratory flow measurements that may be caused by "noise", such as is attributable to respiratory circuit leaks, signal drift, a non-unity respiratory quotient, or another respiratory flow error-inducing factor. The method includes monitoring the respiratory flow and carbon dioxide of the patient during at least a portion of both inspiration and expiration; calculating an inspiratory tidal volume, an inspiratory volume averaged carbon dioxide fraction, an expiratory tidal volume, and an expiratory volume averaged carbon dioxide fraction; and selecting a tidal volume to replace at least one of the inspiratory tidal volume and the expiratory tidal volume. The carbon dioxide elimination of the patient is then calculated with the select tidal volume, the inspiratory volume averaged carbon dioxide fraction, and the expiratory volume averaged carbon dioxide fraction.

20 Claims, 3 Drawing Sheets

OTHER PUBLICATIONS

Fick, A., Über die Messung des Blutquantums in den Herzventrikeln, Sitzungsbericht der Physikalisch–Medizinischen Gesellschaft zu Würzburg (1870) 36 (2 pages).

Gama de Abreu, Marcelo, et al., Measurement of Pulmonary Capillary Blood Flow for Trending Mixed Venous Blood Oxygen Saturation and Oxygen Delivery, Crit. Care Med. (1998), vol. 26, No. 1 (Suppl.), A106, Abstract #238, (1 page).

Gama de Abreu, Marcelo, et al., Is the Partial $CO_2$ Rebreathing Technique a Useful Tool for Trending Pulmonary Capillary Blood Flow During Adjustments of Peep?, Crit. Care Med. (1998), vol. 26, No. 1 (Suppl.), A106, Abstract #237, (1 page).

Gama de Abreu, et al., Partial carbon dioxide rebreathing: A reliable technique for noninvasive measurement of non-shunted pulmonary capillary blood flow, Crit. Care Med. (1997) 25(4):675–83.

Gedeon, A., et al., Noninvasive Cardiac Output Determined with a New Method Based on Gas Exchange Measurements and Carbon Dioxide Rebreathing: A Study in Animals/Pigs, J. Clin. Monit. (1992) 8(4):267–78.

Gedeon, A., et al., A new method for noninvasive bedside determination of pulmonary blood flow, Med. & Biol. Eng. & Comput. (1980) 18:411–418.

Guyton, A.E., et al., Measurement of cardiac output by the direct Fick method, In: Cardiac output and its regulation, W.B. Saunders Company (1973) 21–39.

Kyoku, I., et al., Measurement of cardiac output by Fick method using $CO_2$ analyzer Servo, Kyobu Geka, Japanese Journal of Thoracic Surgery (1988) 41(12):966–70.

Lynch, J., et al., Comparison of a modified Fick method with thermodilution for determining cardiac output in critically ill patients on mechanical ventilation, Intensive Care Med. (1990) 16:248–51.

Mahutte, C. Kees, et al., Relationship of Thermodilution Cardiac Output to Metabolic Measurements and Mixed Venous Oxygen Saturation, Chest (1993) 104(4):1236–42.

Miller, D.M., et al., A Simple Method for the Continuous Noninvasive Estimate of Cardiac Output Using the Maxima Breathing System. A Pilot Study, Anaesth. Intens. Care (1997) 25(1):23–28.

Österlund, B., et al., A new method of using gas exchange measurements for the noninvasive determination of cardiac output: clinical experiences in adults following cardiac surgery, Acta Anaesthesiol Scand (1995) 39:727–32.

Sackner, Marvin A., Measurement of cardiac output by alveolar gas exchange, Handbook of Physiology—The Respiratory System IV, Chapter 13, 233–55.

Spalding, H.K., et al., Carbon Dioxide ($CO_2$) Elimination Rate Accurately Predicts Cardiac Output, Anesthesiology (1997) 87(3A) (1 page).

Sprung, Charles L., et al., Ventricular Arrhythmias During Swan–Ganz Catheterization of the Critically Ill, Chest (1981) 79:413–15.

Taskar, V., et al., Dynamics of Carbon Dioxide Elimination Following Ventilator Resetting, Chest (1995) 108:196–202.

Winkler, Tilo, et al., Pulmonary Capillary Blood Flow by Partial $CO_2$ Rebreathing: A Simulation Study Using a Bicompartmental Model of Gas Exchange, Crit. Care Med. (1998), vol. 26, No. 1 (Suppl.), A105, Abstract #234, (1 page).

ISO-VOLUMETRIC METHOD OF MEASURING CARBON DIOXIDE ELIMINATION

BACKGROUND OF THE INVENTION

1. Field of the Invention

The present invention relates to methods of measuring carbon dioxide elimination. Particularly, the present invention relates to a method of measuring carbon dioxide elimination that compensates for "noise" in respiratory flow measurements, such as leaks in a breathing circuit or system drift, that causes inaccuracies in tidal volume and carbon dioxide elimination calculations and may cause inconsistencies between carbon dioxide elimination calculations.

2. Background of Related Art

Carbon dioxide elimination ($VCO_2$) is the volume of carbon dioxide ($CO_2$) excreted from the body of a patient during respiration. Conventionally, carbon dioxide elimination has been employed as an indicator of metabolic activity. Carbon dioxide elimination has also been used in re-breathing methods of determining pulmonary capillary blood flow and cardiac output.

The carbon dioxide Fick equation:

$$Q = VCO_2 / (CvCO_2 - CaCO_2),$$

where Q is cardiac output, $CvCO_2$ is carbon dioxide content of the venous blood of the patient, and $CaCO_2$ is the carbon dioxide content of the arterial blood of the patient, has been employed to non-invasively determine the cardiac output of a patient. The carbon dioxide elimination of the patient may be non-invasively measured as the difference per breath between the volume of carbon dioxide inhaled during inspiration and the volume of carbon dioxide exhaled during expiration, and is typically calculated as the integral of the carbon dioxide signal, or the fraction of respiratory gases that comprises carbon dioxide or "carbon dioxide fraction", times the rate of flow over an entire breath. The volume of carbon dioxide inhaled and exhaled may each be corrected for any deadspace or intrapulmonary shunt.

The partial pressure of end tidal carbon dioxide ($PetCO_2$ or $etCO_2$) is also measured in re-breathing processes. The partial pressure of end-tidal carbon dioxide, after correcting for any deadspace, is typically assumed to be approximately equal to the partial pressure of carbon dioxide in the alveoli ($PACO_2$) of the patient or, if there is no intrapulmonary shunt, the partial pressure of carbon dioxide in the arterial blood of the patient ($PaCO_2$).

Re-breathing is typically employed either to non-invasively estimate the carbon dioxide content of mixed venous blood (in total re-breathing) or to obviate the need to know the carbon dioxide content of the mixed venous blood (by partial re-breathing). Re-breathing processes typically include the inhalation of a gas mixture that includes carbon dioxide. During re-breathing, the carbon dioxide elimination of the patient is less than during normal breathing. Re-breathing during which the carbon dioxide elimination decreases to near zero is typically referred to as total re-breathing. Re-breathing that causes some decrease, but not a total cessation of carbon dioxide elimination, is typically referred to as partial re-breathing.

Figure 1:
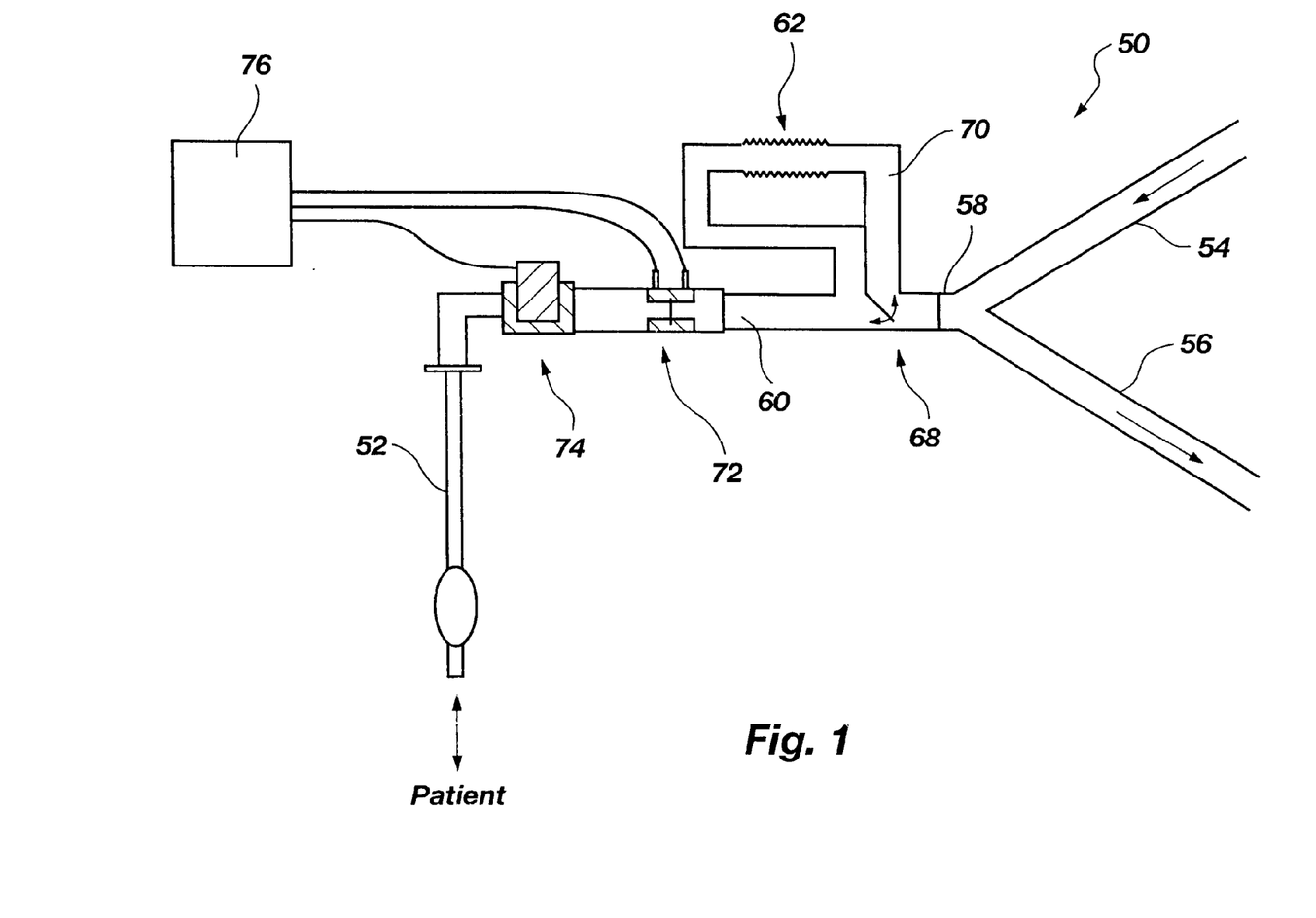
FIG. 1 is a schematic representation of an exemplary re-breathing circuit that may be employed with the methods of the present invention.

Re-breathing is typically conducted with a re-breathing circuit, which causes a patient to inhale a gas mixture that includes carbon dioxide. FIG. 1 schematically illustrates an exemplary re-breathing circuit 50 that includes a tubular airway 52 that communicates air flow to and from the lungs of a patient. Tubular airway 52 may be placed in communication with the trachea of the patient by known intubation processes, or by connection to a breathing mask positioned over the nose and/or mouth of the patient. A flow meter 72, which is typically referred to as a pneumotachometer, and a carbon dioxide sensor 74, which is typically referred to as a capnometer, are disposed between tubular airway 52 and a length of hose 60, and are exposed to any air that flows through re-breathing circuit 50. Both ends of another length of hose, which is referred to as deadspace 70, communicate with hose 60. The two ends of deadspace 70 are separated from one another by a two-way valve 68, which may be positioned to direct the flow of air through deadspace 70. Deadspace 70 may also include an expandable section 62. A Y-piece 58, disposed on hose 60 opposite flow meter 72 and carbon dioxide sensor 74, facilitates the connection of an inspiratory hose 54 and an expiratory hose 56 to re-breathing circuit 50 and the flow communication of the inspiratory hose 54 and expiratory hose 56 with hose 60. During inhalation, gas flows into inspiratory hose 54 from the atmosphere or a ventilator (not shown). During normal breathing, valve 68 is positioned to prevent inhaled and exhaled air from flowing through deadspace 70. During re-breathing, valve 68 is positioned to direct the flow of exhaled and inhaled gases through deadspace 70.

As the amount of carbon dioxide in the re-breathed gas mixture typically approximates the expected carbon dioxide content of the patient's venous blood, the re-breathed air, which is inhaled from deadspace 70 during re-breathing, includes air that has been exhaled by the patient (i.e., carbon dioxide-rich air).

During total re-breathing, substantially all of the gas inhaled by the patient was expired during the previous breath. Thus, during total re-breathing, the partial pressure of end-tidal carbon dioxide ($PetCO_2$ or $etCO_2$) is typically assumed to be equal to the partial pressure of carbon dioxide in the arterial ($PaCO_2$), venous ($PvCO_2$), or alveolar ($PACO_2$) blood of the patient. Total re-breathing processes are based on the assumption that neither pulmonary capillary blood flow nor the content of carbon dioxide in the venous blood of the patient ($CvCO_2$) changes substantially during the re-breathing process. The partial pressure of carbon dioxide in blood may be converted to the content of carbon dioxide in blood by means of a carbon dioxide dissociation curve. Thus, the carbon dioxide form of the Fick equation, in which $CvCO_2$ and $CaCO_2$ are variables, may be employed to determine cardiac output or pulmonary capillary blood flow.

In partial re-breathing, the patient inhales a mixture of "fresh" gases and gases exhaled during the previous breath. Thus, the patient does not inhale as much carbon dioxide as would be inhaled during a total re-breathing process. Conventional partial re-breathing processes typically employ a differential form of the carbon dioxide Fick equation to determine the pulmonary capillary blood flow or cardiac output of the patient, which do not require knowledge of the carbon dioxide content of the mixed venous blood. This differential form of the carbon dioxide Fick equation considers measurements of carbon dioxide elimination, $CvCO_2$, and the content of carbon dioxide in the alveolar blood of the patient ($CACO$) during both normal breathing and the re-breathing process as follows:

$$Q_{pcbf\,BD} = \frac{VCO_{2B} - VCO_{2D}}{(CvCO_{2B} - CvCO_{2D}) - (CaCO_{2B} - CaCO_{2D})},$$

where $V_{CO_{2B}}$ and $V_{CO_{2D}}$ are the carbon dioxide production of the patient before re-breathing and during the re-breathing process, respectively, $CvCO_{2B}$ and $CvCO_{2D}$ are the content of $CO_2$ of the venous blood of the patient before re-breathing and during the re-breathing process, respectively, and $CaCO_{2B}$ and $CaCO_{2D}$ are the content of $CO_2$ in the arterial blood of the patient before re-breathing and during re-breathing, respectively.

Alternative differential Fick methods of measuring pulmonary capillary blood flow or cardiac output have also been employed. Such differential Fick methods typically include a brief change of $PetCO_2$ and $V_{CO_2}$ in response to a change in effective ventilation. This brief change can be accomplished by adjusting the respiratory rate, inspiratory and/or expiratory times, or tidal volume. A brief change in effective ventilation may also be effected by adding $CO_2$, either directly or by re-breathing. An exemplary differential Fick method that has been used, which is disclosed in Gedeon, A. et al. in 18 *Med. & Biol. Eng. & Comput.* 411–418 (1980), employs a period of increased ventilation followed immediately by a period of decreased ventilation.

The carbon dioxide elimination of a patient is typically measured over the course of a breath by the following, or an equivalent, equation:

$$V_{CO_2} = \int_{breath} Vf_{CO_2}\, dt,$$

where V is the measured respiratory flow and $f_{CO_2}$ is the substantially simultaneously detected carbon dioxide signal, or fraction of the respiratory gases that comprises carbon dioxide or "carbon dioxide fraction".

Due to inaccuracies in respiratory flow measurements, accurate, consistent carbon dioxide elimination measurements are, however, somewhat difficult to obtain. Inaccurate flow measurements may be caused by leaks in the breathing circuit, drift of the baseline respiratory flow value, a non-unity respiratory quotient (RQ) (i.e., RQ is not equal to one), or other error-inducing factors, which are collectively referred to as "noise". Moreover, noise may have different and inconsistent effects on inspiratory flow and expiratory flow.

Breathing circuit leaks, such as endotracheal tube cuff leaks, or simply "cuff leaks", are a significant cause of noise when monitoring the respiration of neonates. The component of a flow monitor that senses expiratory flow may be connected directly to an endotracheal tube cuff, where the endotracheal tube may connect to or adjacent a tube with a different inner diameter. As the patient exhales, gas may escape through leaks around the endotracheal tube cuff and may, therefore, not be measured by the expiratory flow sensor. Differences in the internal diameters in the adjacent, connected tubes may also affect the flow of respiratory gases through the tube. Accordingly, the expiratory flow measurement may be inaccurate.

Inspiratory flow measurements are less affected by changes in inlet conditions, flow rate, or the escape of air around the cuff. Moreover, inspired gases are typically drier and include fewer particulates than expired gases. Accordingly, with respect to noise, inspiratory flow measurements are typically more reliable and accurate than expiratory flow measurements. For the same reasons, the volume of gas inhaled by the patient may be calculated with greater reliability and accuracy than the volume of gas exhaled by the patient.

When the preceding equation is employed to calculate the carbon dioxide elimination of the patient from the respiratory flow and carbon dioxide fraction measurements over an entire breath, such noise-induced inaccuracies in either the expiratory flow, the inspiratory flow, or both may cause inaccuracies in the carbon dioxide elimination determination or inconsistencies between carbon dioxide elimination determinations.

Accordingly, there is a need for a method of consistently and accurately calculating carbon dioxide elimination in the presence of noise relative to the consistency and accuracy of conventional methods.

SUMMARY OF THE INVENTION

The method of the present invention addresses the foregoing needs.

The method of the present invention includes measuring the flow (V) and the fraction of respiratory gases that comprise carbon dioxide ($f_{CO_2}$), which is also referred to as the carbon dioxide fraction, during both inspiration (i) and expiration (e). The inspiratory tidal volume ($V_i$) and expiratory tidal volume ($V_e$) are then calculated, as known in the art, from the flow and carbon dioxide fraction measurements. The average fraction of respiratory gases that comprises carbon dioxide during each of inspiration and expiration, which may also be referred to as the volume averaged fractions of carbon dioxide, are also calculated.

When noise affects respiratory flow measurements, inspiratory tidal volume calculations or expiratory tidal volume calculations and, therefore, carbon dioxide elimination calculations may be inaccurate or inconsistent. Preferably, the method of the present invention at least partially counteracts, or "corrects", such noise-induced inaccuracies or inconsistencies. The inspiratory tidal volume, expiratory tidal volume, or some value between the inspiratory tidal volume and expiratory tidal volume, such as an arithmetic or weighted average, is selected as the tidal volume ($V_t$) to be employed in calculating the carbon dioxide elimination according to the method of the present invention. The selected $V_t$ value is preferably a more accurate tidal volume than at least one of the inspiratory tidal volume and the expiratory tidal volume.

The carbon dioxide elimination of the patient then may be calculated using the following equation:

$$V_{CO_2} = V_t(f_e - f_i),$$

where $f_i$ is the volume averaged fraction of inhaled respiratory gases that comprises carbon dioxide, or the volume averaged inspiratory fraction of carbon dioxide, $f_e$ is the volume averaged fraction of exhaled respiratory gases that comprises carbon dioxide, or the volume averaged expiratory fraction of carbon dioxide. In the preceding equation, preferably at least one of the inspiratory component and expiratory component is modified to counteract any noise-induced inaccuracy or inconsistency in that component.

The manner in which at least one of the components of the carbon dioxide elimination calculation is modified is illustrated by the derivations of the preceding equation that follow. As is known in the art, $$V_i f_i = \int_i Vf_{CO_2}\, dt \text{ and}$$

$$V_e f_e = \int_e Vf_{CO_2}\, dt.$$

Accordingly, $$f_i = \frac{\int_i V f_{CO2} dt}{V_i}$$

and $$f_e = \frac{\int_e V f_{CO2} dt}{V_e};$$

thus, the two preceding equations $f_i$ and $f_e$ may be substituted into $$V_{CO_2} = V_t \cdot (f_e - f_i)$$

to yield the following equation:

$$V_{CO_2} = V_t \cdot ((\int_e V f_{CO2}\, dt/V_e) - (\int_i V f_{CO2}\, dt/V_i)).$$

The preceding equation may be rewritten as:

$$V_{CO_2} = (V_t/V_e \cdot (\int_e V f_{CO2}\, dt)) - (V_t/V_i \cdot (\int_i V f_{CO2})).$$

Thus, if the tidal volume employed to calculate the carbon dioxide elimination of the patient is the inspiratory tidal volume (i.e., $V_t = V_i$), then the preceding equation yields:

$$V_{CO_2} = (V_i/V_e \cdot (\int_e V f_{CO2}\, dt)) - \int_i V f_{CO2}.$$

If the tidal volume employed in the carbon doxide elimination calculation is the expiratory tidal volume (i.e., $V_t = V_e$), then the carbon dioxide elimination of the patient may be calculated by the following equation:

$$V_{CO_2} = \int_e V f_{CO2}\, dt - (V_e/V_i \cdot (\int_i V f_{CO2})).$$

As the three preceding equations illustrate, when the same type of tidal volume measurement is employed with each calculation of carbon dioxide elimination, the inspiratory component of respiration, the expiratory component of respiration, or both components are modified by the ratio of the tidal volume employed to the inspimatory tidal volume or the ratio of the tidal volume employed to the expiratory tidal volume. Since these ratios may be assumed to remain substantially constant in the presence of noise, the calculation of carbon dioxide elimination in accordance with the method of the present invention is substantially consistent between different carbon dioxide elimination measurements. Moreover, as the method of the present invention preferably includes selecting an accurate tidal volume for use in the calculation of carbon dioxide elimination, either the inspiratory component of the equation, the expiratory component of the equation, or both may yield a more accurate carbon dioxide elimination value.

Other advantages of the methods of the present invention will become apparent through a consideration of the ensuing description, the accompanying drawings, and the appended claims.

DETAILED DESCRIPTION OF THE PREFERRED EMBODIMENTS

Figure 2:
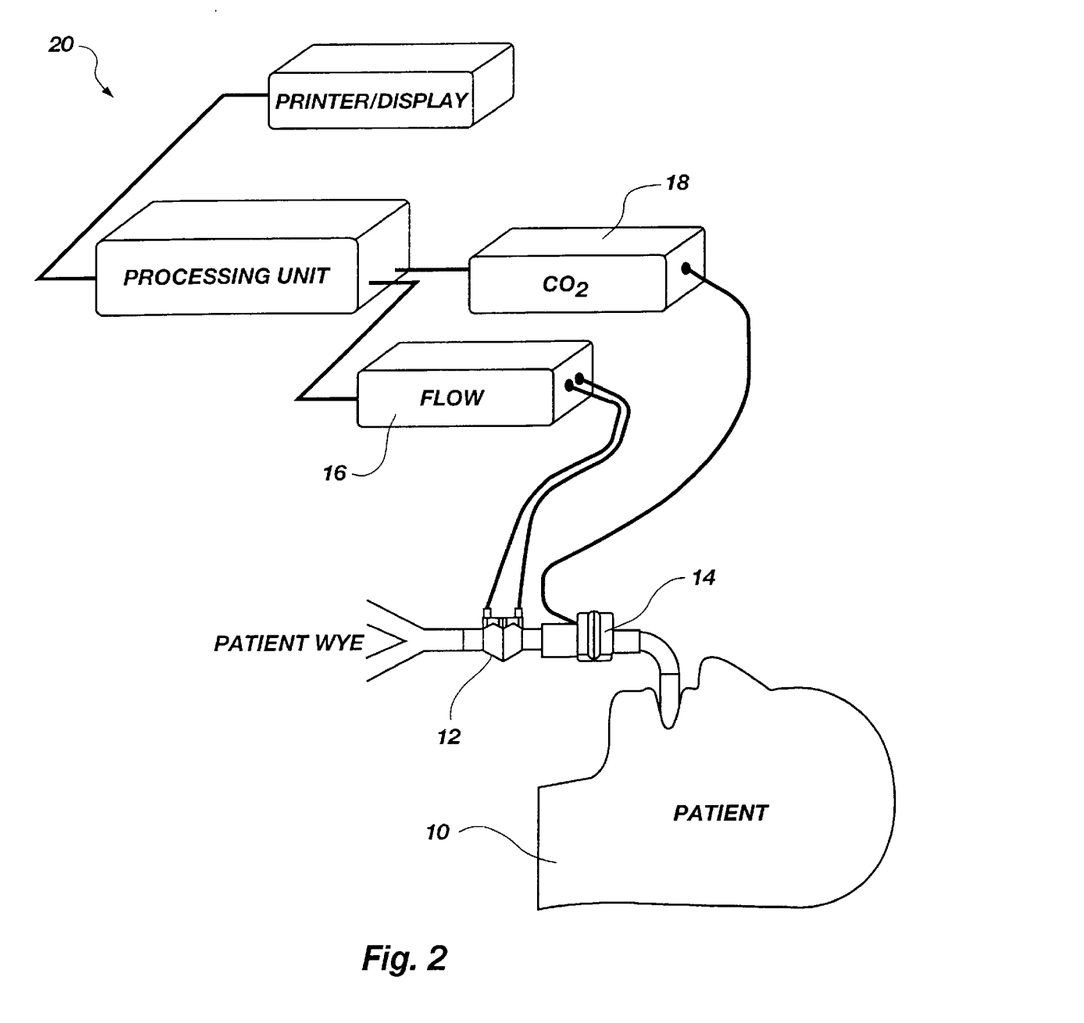
FIG. 2 is a schematic representation which illustrates the componentry that may be utilized to measure respiratory profile parameters that are employed in the methods of the present invention.

With reference to FIG. 2, a preferred embodiment of the method of the present invention includes non-invasively measuring the flow rates and $CO_2$ concentration of gas mixtures that are inhaled and exhaled by a patient 10 over the course of the patient's breathing, such as during normal respiration or during known re-breathing techniques. A flow sensor 12 of a known type, such as the differential-pressure type respiratory flow sensors manufactured by Novametrix Medical Systems Inc. ("Novametrix") of Wallingford, Conn. (e.g, the Pediatric/Adult Flow Sensor (Catalog No. 6717) or the Neonatal Flow Sensor (Catalog No. 6718)), which may be operatively attached to a ventilation apparatus (not shown), as well as respiratory flow sensors based on other operating principles and manufactured or marketed by others, may be employed to measure the flow rates of the breathing of patient 10.

A $CO_2$ sensor 14, such as the CAPNOSTART® $CO_2$ sensor and a complementary airway adapter (e.g., the Pediatric/Adult Single Patient Use Airway Adapter (Catalog No. 6063), the Pediatric/Adult Reusable Airway Adapter (Catalog No. 7007), or the Neonatal/Pediatric Reusable Airway Adapter (Catalog No. 7053)), which are manufactured by Novametrix, as well as main stream and side stream $CO_2$ sensors manufactured or marketed by others, may be employed to measure the $CO_2$ concentration of gas mixtures that are inhaled and exhaled by patient 10.

Flow sensor 12 and $CO_2$ sensor 14 are connected to a flow monitor 16 and a $CO_2$ monitor 18, respectively, each of which may be operatively associated with a computer 20 so that data from the flow and $CO_2$ monitors 16 and 18 representative of the signals from each of flow sensor 12 and $CO_2$ sensor 14 may be detected by computer 20 and processed according to programming (e.g., by software) thereof. Preferably, raw flow and $CO_2$ signals from the flow monitor and $CO_2$ sensor are filtered to remove any significant artifacts. As respiratory flow and $CO_2$ pressure measurements are made, the respiratory flow and $CO_2$ pressure data may be stored by computer 20.

Each breath, or breathing cycle, of patient 10 may be delineated as known in the art, such as by continuously monitoring the flow rate of the breathing of patient 10.

Figure 3:
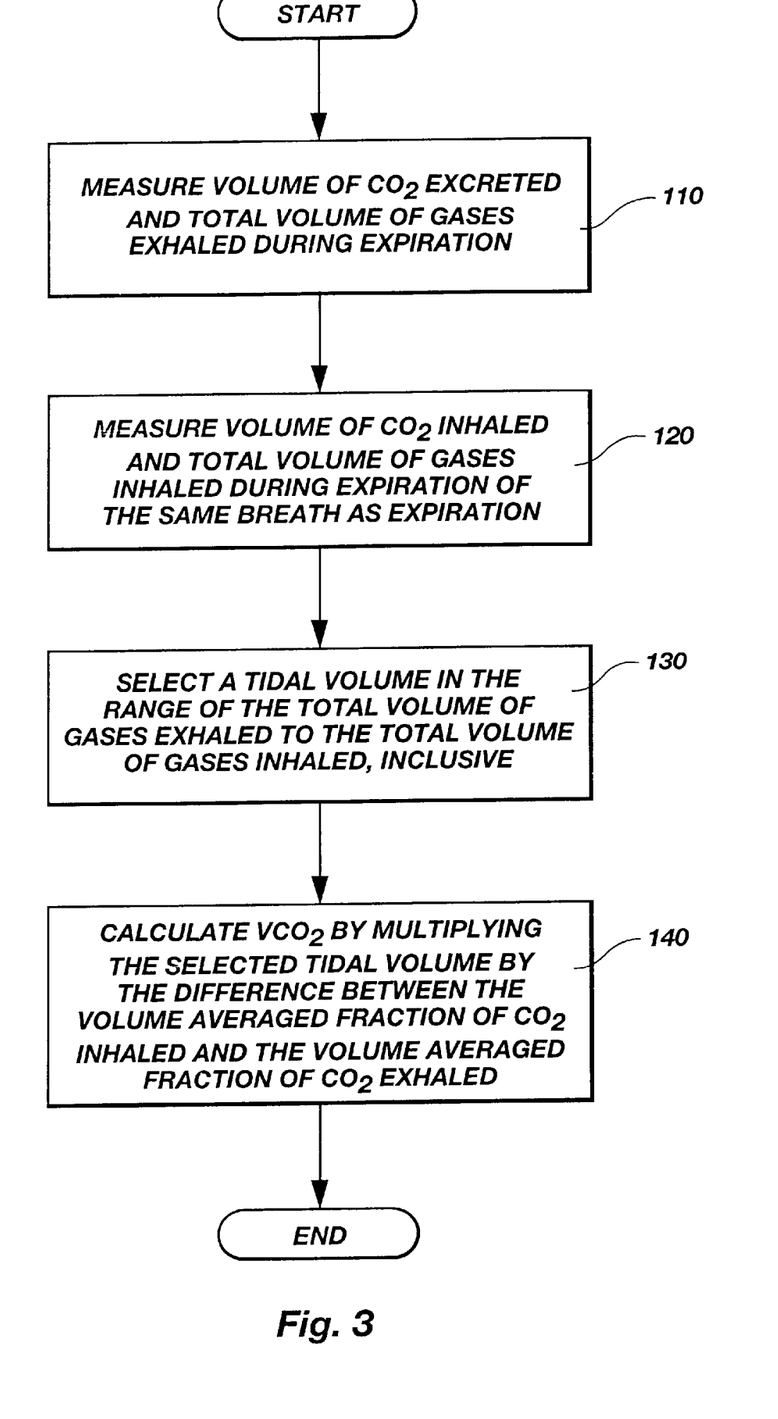
FIG. 3 is a flow chart illustrating a preferred embodiment of the method of the present invention.

With reference to FIG. 3, at references 120 and 110, the flow signals or measurements of each of the inspiratory and expiratory phases of each breathing cycle may be employed, as known in the art, to determine the tidal volume of gases inhaled by the patient, or the inspiratory tidal volume ($V_i$), at reference 120, and the tidal volume of gases exhaled by the patient, or the expiratory tidal volume ($V_e$), at reference 110, respectively.

The carbon dioxide signals or measurements, which include the fraction of respiratory gases that comprises carbon dioxide or "carbon dioxide fraction", and the flow signals or measurements of each of the inspiratory and expiratory phases of each breathing cycle may then be employed, as known in the art, at references 120 and 110, respectively, of FIG. 3, to determine the average fraction of inspired gases of a breath that comprises carbon dioxide ($f_i$), or volume averaged inspiratory carbon dioxide fraction, at reference 120, as follows:

$$f_i = \frac{\int_i V f_{CO2}}{\int_i V}$$

and the average fraction of expired gases of a breath that comprises carbon dioxide ($f_e$), or volume averaged expiratory carbon dioxide fraction, at reference 110, as follows:

$$f_e = \frac{\int_e V f_{CO2}}{\int_e V},$$

where i represents signals or measurements obtained during inspiration and e represents signals or measurements obtained during expiration. Errors in the flow signal during either inspiration or expiration will cancel out since flow signals are employed in both the numerator and denominator of the two preceng equations. Consequently, calculation of the volume averaged fractions of inspired or expired carbon dioxide are not affected by cuff leaks or other noise that may create errors in the measurement of respiratory flow.

Alternatively, the carbon dioxide signals or measurements and the flow signals or measurements may be employed to calculate the volume of carbon dioxide inhaled by the patient ($V_{CO2i}$), as follows:

$$V_{CO2i} = \int_i V f_{CO2} \, dt$$

and the volume of carbon dioxide exhaled by the patient ($V_{CO2e}$), as follows:

$$V_{CO2e} = \int_e V f_{CO2} dt.$$

The average fraction of inspired gases of a breath that comprises carbon dioxide ($f_i$) may then be calculated, as known in the art, such as from the volume of carbon dioxide inhaled and the inspiratory tidal volume. The average fraction of expired gases that comprises carbon dioxide ($f_e$) may be similarly calculated, as known in the art, such as from the volume of carbon dioxide exhaled and the expiratory tidal volume. The tidal volume and average carbon dioxide fraction measurements may be subsequently employed to calculate the carbon dioxide elimination of the patient.

The carbon dioxide elimination of a patient is typically calculated as the integral of flow and the carbon dioxide fraction of the breath over the course of an entire breath in accordance with the following equation:

$$V_{CO2} = \int_{breath} V f_{CO2} dt,$$

where V represents air flow measurements during the breath and $f$ represents measurements of the fraction of the breath that comprises carbon dioxide.

According to the method of the present invention, the preceding equation is separated into an inspiratory component and an expiratory component, as follows:

$$V_{CO2} = \int_e V f_{CO2} \, dt - \int_i V f_{CO2} dt.$$

The carbon dioxide elimination calculation is separated or isolated into an inspiratory component and an expiratory component since, during the presence of cuff leaks or other noise, any errors in the flow measurements may differ between inspiration and expiration. Thus, one of the inspiratory flow and expiratory flow may be less affected than the other by an error.

As known in the art, the preceding equation may be rewritten in terms of the expiratory tidal volume, the inspiratory tidal volume, the volume averaged fraction of carbon dioxide exhaled by the patient ($f_e$), and the volume averaged fraction of carbon dioxide inhaled by the patient ($f_i$). Thus, the carbon dioxide elimination of the patient may be calculated by the following equation:

$$V_{CO2} = (V_e \cdot f_e) - (V_i \cdot f_i).$$

In accordance with the method of the present invention, at reference 130 of FIG. 3, an assumption is made that the inspiratory tidal volume of a patient during a breath is substantially equal to the expiratory tidal volume of the patient during the same breath. Accordingly, the following equation may be employed to calculate the carbon dioxide elimination of a patient, at reference 140 of FIG. 3, in accordance with the method of the present invention:

$$V_{CO2} = (V_t \cdot f_e) - (V_t \cdot f_i),$$

from which $V_t$ may be factored to provide the following:

$$V_{CO2} = V_t (f_e - f_i),$$

where $V_t$ is a tidal volume of the patient's breathing.

The actual tidal volume of a patient's inspiration or expiration may, however, be difficult to accurately measure due to the presence of a cuff leak or other noise. Accordingly, the method of the present invention includes employing a tidal volume value that improves consistency between carbon dioxide elimination measurements and that preferably increases the accuracy with which carbon dioxide elimination is measured during the presence of a cuff leak or other noise.

Since measured expiratory air flow is typically reduced in comparison to actual expiratory air flow during the presence of cuff leaks, and since cuff leaks have little or no effect on inspiratory air flow measurements, the actual volume of a patient's respiration may be the measured inspiratory tidal volume, the measured expiratory tidal volume, or somewhere in between the measured inspiratory tidal volume and the measured expiratory tidal volume. Thus, according to the method of the present invention, the inspiratory tidal volume, the expiratory tidal volume, or another tidal volume that represents the volume of gases inhaled or exhaled by the patient, such as an arithmetic or weighted average of the inspiratory tidal volume and the expiratory tidal volume over at least a portion of one or more breaths, may be selected to represent $V_t$. Preferably, the selected $V_t$ value is a more accurate representation of tidal volume than at least one of the inspiratory tidal volume and the expiratory tidal volume. Since cuff leaks have little or no effect on inspiratory air flow measurements, and since inspiratory tidal volume measurements are typically accurate, the inspiratory tidal volume ($V_i$) is preferably employed as $V_t$ in the method of the present invention. In order to ensure consistent carbon dioxide elimination calculations, the same type of $V_t$ measurement is employed in each calculation of carbon dioxide elimination.

When the inspiratory tidal volume or a tidal volume between the inspiratory tidal volume and the expiratory tidal volume is used as $V_t$, due to any cuff leaks or other noise, the volume measurement may also be a more accurate representation of the actual tidal volume than the measured expiratory tidal volume.

Although the foregoing description contains many specifics, these should not be construed as limiting the scope of the present invention, but merely as providing illustrations of some of the presently preferred embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions and modifications to the invention as disclosed herein which fall within the meaning and scope of the claims are to be embraced thereby.

What is claimed is:

1. A method of determining a carbon dioxide elimination ($V_{CO_2}$) of a patient, comprising:
   sensing a flow of respiration of the patient over at least a portion of at least one breath;
   sensing a carbon dioxide fraction ($f$) of said respiration over said at least a portion;
   selecting a tidal volume ($V_t$) not equal to at least one of an inspiratory tidal volume ($V_i$) and an expiratory tidal volume ($V_e$) of the patient; and
   calculating the carbon dioxide elimination with said flow, said carbon dioxide fraction, and said selected tidal volume.

2. The method of claim 1, wherein said sensing said flow comprises sensing an inspiratory flow during an inspiratory phase of said respiration and said sensing said carbon dioxide fraction comprises sensing an inspiratory carbon dioxide fraction during said inspiratory phase.

3. The method of claim 2, further comprising calculating an inspiratory volume averaged carbon dioxide fraction with said inspiratory flow and said inspiratory carbon dioxide fraction.

4. The method of claim 1, wherein said sensing said flow comprises sensing an expiratory flow during an expiratory phase of said respiration and said sensing said carbon dioxide fraction comprises sensing an expiratory carbon dioxide fraction during said expiratory phase.

5. The method of claim 4, further comprising calculating an expiratory volume averaged carbon dioxide fraction with said expiratory flow and said expiratory carbon dioxide fraction.

6. The method of claim 1, wherein said selecting said tidal volume comprises selecting said inspiratory tidal volume.

7. The method of claim 1, wherein said selecting said tidal volume comprises selecting said expiratory tidal volume.

8. The method of claim 1, wherein said selecting said tidal volume comprises selecting a value between said inspiratory tidal volume and said expiratory tidal volume.

9. The method of claim 1, wherein said selecting said tidal volume comprises calculating an arithmetic average of said inspiratory tidal volume and said expiratory tidal volume.

10. The method of claim 1, wherein said selecting said tidal volume comprises calculating a weighted average of said inspiratory tidal volume and said expiratory tidal volume.

11. The method of claim 1, further comprising:
    calculating an inspiratory volume averaged carbon dioxide fraction ($f_i$) with said flow and said carbon dioxide fraction;
    calculating an expiratory volume averaged carbon dioxide fraction ($f_e$) with said flow and said carbon dioxide fraction; and
    employing the following equation to effect said calculating the carbon dioxide elimination:

$$V_{CO_2} = V_t \cdot (f_e - f_i).$$

12. The method of claim 1, further comprising:
    calculating an inspiratory volume averaged carbon dioxide fraction ($f_i$) with said flow and said carbon dioxide fraction;
    calculating an expiratory volume averaged carbon dioxide fraction ($f_e$) with said flow and said carbon dioxide fraction; and
    employing the following equation to effect said calculating the carbon dioxide elimination:

$$V_{CO_2} = (V_t/V_e \cdot (\int_e V f_{CO_2} dt)) - (V_t/V_i \cdot (\int_i V f_{CO_2})).$$

13. A method of calculating a carbon dioxide elimination ($V_{CO_2}$) of a patient, comprising:
    obtaining a plurality of inspiratory flow signals of the patient;
    obtaining a plurality of expiratory flow signals of the patient;
    selecting a select tidal volume ($V_t$) based at least in part on one of an inspiratory tidal volume ($V_i$) and an expiratory tidal volume ($V_e$); and
    calculating the carbon dioxide elimination with said plurality of inspiratory flow signals, said plurality of expiratory flow signals, and said select tidal volume.

14. The method of claim 13, further comprising:
    obtaining a plurality of inspiratory carbon dioxide signals substantially simultaneously with said obtaining said plurality of inspiratory flow signals;
    obtaining a plurality of expiratory carbon dioxide signals substantially simultaneously with said obtaining said plurality of expiratory flow signals;
    calculating an inspiratory volume averaged carbon dioxide fraction ($f_i$) with said inspiratory flow signals and said inspiratory carbon dioxide signals;
    calculating an expiratory volume averaged carbon dioxide fraction ($f_e$) with said expiratory flow signals and said expiratory carbon dioxide signals; and
    employing the following equation to effect said calculating:

$$V_{CO_2} = V_t \cdot (f_e - f_i).$$

15. The method of claim 13, further comprising:
    obtaining a plurality of inspiratory carbon dioxide signals substantially simultaneously with said obtaining said plurality of inspiratory flow signals;
    obtaining a plurality of expiratory carbon dioxide signals substantially simultaneously with said obtaining said plurality of expiratory flow signals;
    calculating an inspiratory volume averaged carbon dioxide fraction ($f_i$) with said inspiratory flow signals and said inspiratory carbon dioxide signals;
    calculating an expiratory volume averaged carbon dioxide fraction ($f_e$) with said expiratory flow signals and said expiratory carbon dioxide signals; and
    employing the following equation to effect said calculating:

$$V_{CO_2} = (V_t/V_e \cdot (\int_e V f_{CO_2} dt)) - (V_t/V_i \cdot (\int_i V f_{CO_2})).$$

16. The method of claim 13 wherein said select tidal volume comprises said inspiratory tidal volume.

17. The method of claim 13, wherein said select tidal volume comprises said expiratory tidal volume.

18. The method of claim 13, wherein said select tidal volume comprises a value between said inspiratory tidal volume and said expiratory tidal volume.

19. The method of claim 13, wherein said select tidal volume comprises an arithmetic average of said inspiratory tidal volume and said expired tidal volume.

20. The method of claim 13, wherein said select tidal volume comprises a weighted average of said inspiratory tidal volume and said expired tidal volume.

* * * * *

UNITED STATES PATENT AND TRADEMARK OFFICE
CERTIFICATE OF CORRECTION

PATENT NO.     : 6,059,732
DATED          : May 9, 2000
INVENTOR(S)    : Joseph A. Orr et al.

It is certified that error appears in the above-identified patent and that said Letters Patent is hereby corrected as shown below:

Drawings,
Figure 1, remove "76" and its corresponding lead line as shown on the attached page.

Column 2,
Line 67, change "(CACO)" to -- (CACO2) --

Column 10,
Lines 63 and 66, change "expired" to -- expiratory --

UNITED STATES PATENT AND TRADEMARK OFFICE
CERTIFICATE OF CORRECTION

PATENT NO.    : 6,059,732
DATED         : May 9, 2000
INVENTOR(S)   : Joseph A. Orr et al.

It is certified that error appears in the above-identified patent and that said Letters Patent is hereby corrected as shown below:

Signed and Sealed this

Fifteenth Day of July, 2003

JAMES E. ROGAN
*Director of the United States Patent and Trademark Office*